United States Patent
Von Melchner et al.

(10) Patent No.: US 6,303,327 B1
(45) Date of Patent: Oct. 16, 2001

(54) GENE TRAP CONSTRUCT FOR IDENTIFICATION AND ISOLATION OF GENES

(75) Inventors: Harald Von Melchner; Dieter Hölzer, both of Universitätsklinikum, Abteilung Hämatologie, Theodor-Stern-Kai 7, D-60596 Frankfurt (DE)

(73) Assignees: Harald Von Melchner; Dieter Hölzer, both of Frankfurt (DE)

( * ) Notice: Subject to any disclaimer, the term of this patent is extended or adjusted under 35 U.S.C. 154(b) by 0 days.

(21) Appl. No.: 09/319,495
(22) PCT Filed: Dec. 5, 1997
(86) PCT No.: PCT/EP97/06816
§ 371 Date: Sep. 8, 1999
§ 102(e) Date: Sep. 8, 1999
(87) PCT Pub. No.: WO98/24918
PCT Pub. Date: Jun. 11, 1998

(30) Foreign Application Priority Data

Dec. 6, 1996 (DE) .............................. 196 50 714

(51) Int. Cl.[7] ..................................... C12Q 1/34
(52) U.S. Cl. .............................. 435/18; 435/6; 435/320.1; 435/325; 435/252.3; 435/254.11; 435/419; 536/23.1; 536/23.2
(58) Field of Search ................................. 536/23.1, 23.2; 435/320.1, 252.3, 254.11, 419, 325, 471, 18, 6

(56) References Cited

U.S. PATENT DOCUMENTS 5,434,066 * 7/1995 Bebee et al. ...................... 435/172.3

OTHER PUBLICATIONS

Anton et al. Site–Specific Recombination Mediated by an Adenovirus Vector Expressing the Cre Recombinase Protein: a Molecular Switch for Control of Gene Expression. J. of Virology (1995) 69(8): 4600–4606 Aug. 1995.*

Russ et al. Self–Deleting Retrovirus Vectors for Gene Therapy. J. of Virology (1996) 70(8): 4927–4932, Aug. 1995.*

Gottschalk et al. Molecular regulation of the human IL–3 gene: inducible T cell–restricted expression requires intact AP–1 and Elf–1 nuclear protein binding sites. J. Experimental Medicine (1993) 178(5): 1681–1692 (Abstract only) Nov. 1993.*

(List continued on next page.)

Primary Examiner—Ponnathapu Achutamurthy
Assistant Examiner—Kathleen Kerr
(74) Attorney, Agent, or Firm—Bozicevic Field & Francis LLP; Paula A. Borden

(57) ABSTRACT

The invention under consideration concerns a gene-trapping construct containing a first reporter gene which after activation can activate a second reporter gene, and the use of this gene-trapping construct for identification and isolation of genes, especially genes transiently expressed.

The invention under consideration furthermore concerns a cell, preferably a mammalian cell, containing the abovementioned gene-trapping construct. The invention under consideration in addition concerns the use of this mammalian cell for identification and/or isolation of genes, particularly transient genes. Furthermore the invention concerns a vector containing the abovementioned gene-trapping construct, as well as a kit for identification and/or isolation of genes, especially transient genes, that contains at least the abovementioned gene-trapping construct or the abovementioned vector.

In conclusion, the invention under consideration concerns a process for identification and/or isolation of genes, particularly transient genes.

26 Claims, 9 Drawing Sheets

OTHER PUBLICATIONS

Rosetto et al. Signals from the IL–1 receptor homolog, Toll, can Activate an immune response in a Drosophila hemocyte cell line. Biochemical and Biophysical Research Communications (1995) 209(1) 111–116 (Abstract only), Apr. 1995.*

Coffin et al. (1989), "Genetics of Endogenous Murine Leukemia Viruses," *Ann. NY Acad. Sci.*, vol. 567:39–49.

DeGregori et al. (1994), "A Murine Homolog of the Yeast RNA1 Gene is Required for Postimplantation Development," *Genes and Development*, vol. 8:265–276.

Friedrich et al. (1991), "Promoter Traps in Embryonic Stem Cells: A Genetic Screen to Identify and Mutate Developmental Genes in Mice," *Genes and Development*, vol. 5:1513–1523.

Goff (Jun. 1990), "Integration of Retroviral DNA into the Genome of the Infected Cell," *Cancer Cells*, vol. 2(6):172–178.

Gridley et al. (Jun. 1987), "Insertional Mutagenesis in Mice," *TIG*, vol. 3(6):162–166.

Jaenisch et al. (1985), "Retroviruses and Insertional Mutagenesis," *Cold Spring Harbor Symp. Quant. Biol.*, vol. 50:439–445.

Hill et al. (1993), "Gene and Enhancer Trapping: Mutagenic Strategies for Developmental Studies," *Curr. Top. in Dev. Biol.*, vol. 28:181–206.

Hill et al. (1993), "Screening for Novel Pattern Formation Genes Using Gene Trap Approaches," *Methods in Enzymology*, vol. 225:664–681.

Muthuchamy et al. (Jun. 1993), "Developmental Analysis of Tropomyosin Gene Expression in Embryonic Stem Cells and Mouse Embryos," *Molecular and Cellular Biology*, vol. 13(6):3311–3323.

Rappolee et al. (Sep. 1988), "Developmental Expression of PDGF, TGF–α, and TGF–β Genes in Preimplantation Mouse Embryos," *Science*, vol. 241:1823–1825.

Reddy et al. (Aug. 1992), "Fluorescence–Activated Sorting of Totipotent Embryonic Stem Cells Expressing Developmentally Regulated IacZ Fusion Genes," *Proc. Natl. Acad. Sci. USA*, vol. 89:6721–6725.

Rogers et al. (1991), "Specific Expression of a Retinoic Acid–Regulated, Zinc–Finger Gene, Rex–1, in Preimplantation Embryos, Trophoblast and Spermatocytes," *Development*, vol. 113:815–824.

Sandmeyer et al. (1990), "Integration Specificity of Retrotransposons and Retroviruses," *Ann. Rev. Genet.*, vol. 24:491–518.

Schöler et al. (1990), "Oct–4: A Germline–Specific Transcripton Factor Mapping to the Mouse t–Complex," *EMBO Journal*, vol. 9(7):2185–2195.

Sharpe et al. (Dec. 1990), "Regulated Expression of the Small Nuclear Ribonucleoprotein Particle Protein SmN in Embryonic Stem Cell Differentiation," *Molecular and Cellular Biology*, vol. 10(12):6817–6820.

Skarnes et al. (1992), "A Gene Trap Approach in Mouse Embryonic Stem Cells: the IacZ Reporter is Activated by Splicing, Reflects Endogenous Gene Expression, and is Mutagenic in Mice," *Genes and Development*, vol. 6:903–918.

Varmus (Jun. 10, 1988), "Retroviruses," *Science*, vol. 240:1427–1435.

von Melchner (1992), "Selective Disruption of Genes Expressed in Totipotent Embryonal Stem Cells," *Genes and Development*, vol. 6:919–927.

von Melchner (1995), "Gene Entrapment," *Functional Analysis of the Human Genome*, F. Farzane and D.N. Cooper, eds. (Oxford: Bios Scientific Publishers) Chapter 5:109–129.

Withers–Ward et al. (1994), "Distribution of Targets for Avian Retrovirus DNA Integration in Vivo," *Genes and Development*, vol. 8:1473–1487.

* cited by examiner

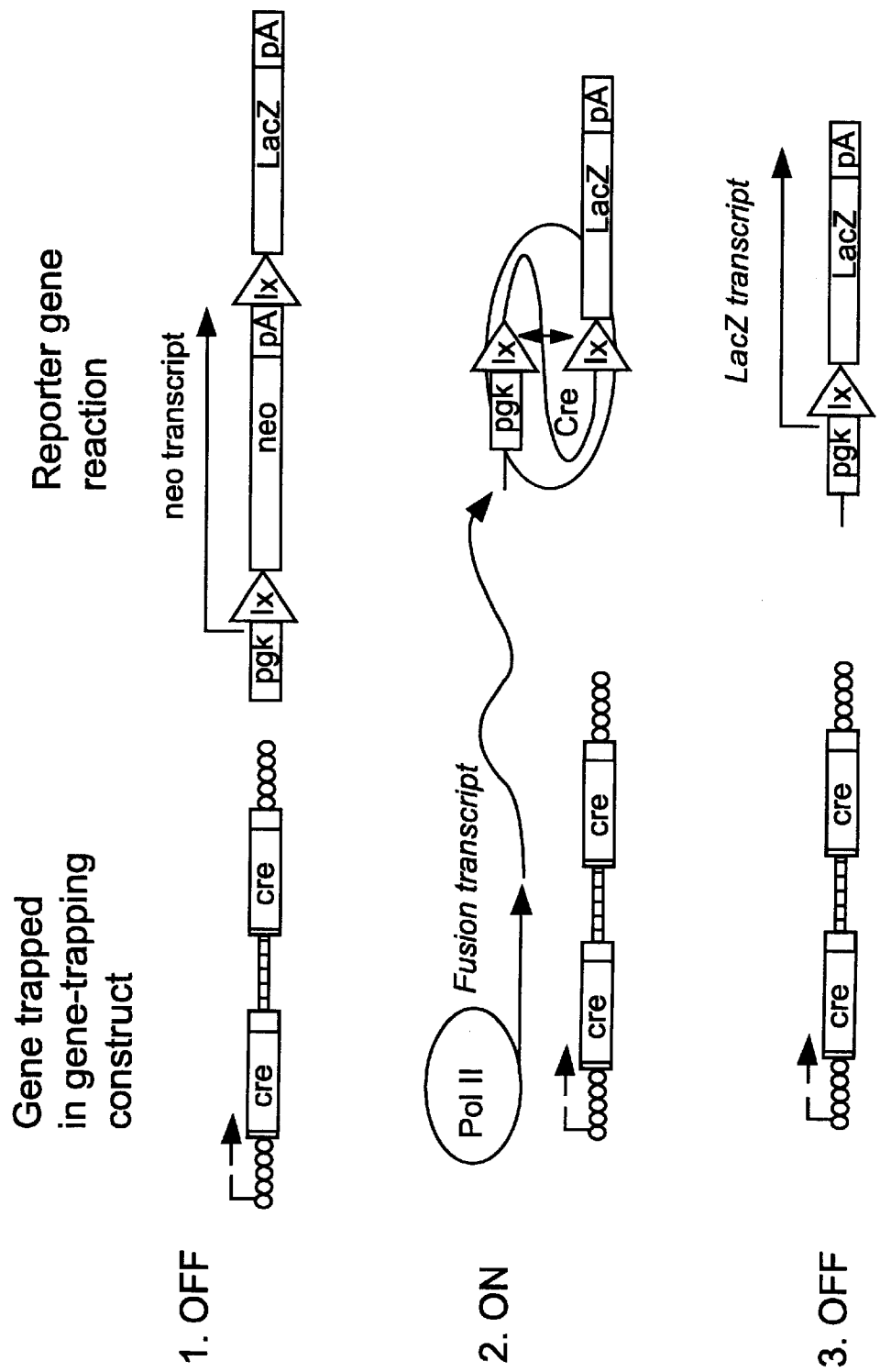

2E12

1C7

8G3

GENE TRAP CONSTRUCT FOR IDENTIFICATION AND ISOLATION OF GENES

CROSS-REFERENCE

This application is a national phase application filed under 35 U.S.C. §371 of International Patent Application No. PCT/EP97/06816, filed Dec. 5, 1997, based on German Patent Application No. DE 19650714.6, filed Dec. 6, 1996, each of which is incorporated herein in its entirety and to which priority is claimed.

FIELD OF THE INVENTION

This invention is in the field of identification of expressed genes.

BACKGROUND OF THE INVENTION

For some years one of the prime objectives of gene technology has been the isolation and identification of genes. For this there is available a whole range of procedures, which have been directed in effect at the isolation, and identification of permanently expressed genes.

The isolation and/or identification of genes which are expressed only transiently, as for example the genes responsible for programmed cell death, cell-cycle genes, DNA repair genes and differentiation-specific genes, is much more difficult.

To identify such genes in mammalian cells, where genetic analysis by the use of Drosophila melanogaster is unsuitable, a process has been developed which is based on the induction of gene fusions between a reporter gene without promoter and the control elements of a cellular gene via specific vectors, which are described as "gene traps" or "promotor traps". Various types of vector have been developed for insertion mutagenesis in mammals, whereby a reporter gene is inserted into the chromosome at a large number of places depending on chance, including in transcriptionally active areas. During selection for gene expression, clones are retained in which the reporter gene is fused with the regulatory elements of an endogenous gene. In this way the vectors act as gene traps and provide a very helpful means for the analysis of gene function (Reviews in Hill & Wurst, 1993; Hill & Wurst 1993; von Melchner et al 1993; von Melchner & Ruley, 1995). In the majority of cases the gene-trapping vectors are transduced as recombinant retroviruses, although electroporated DNA is also used. The retroviruses display the advantage that they integrate in several areas throughout the entire genome and hence scarcely damage the neighbouring DNA (Varmus, 1988; Coffin et al., 1989; Goff, 1990; Sandmeyer et al., 1990; Withers/Ward et al., 1994).

It could be demonstrated that the gene traps are a practical means of analysing gene function in mice. Since totipotent mouse embryonic stem (ES) cells are used as cellular targets, mouse strains displaying inactivated gene function on account of mutations can be constructed. Unlike with gene splitting due to homologous recombination, the gene-trapping processes are not confined to genes, are sustainable for the cloned sequences and hence represent a process for the isolation and identification of genes as yet unknown.

Nevertheless, in order to identify and isolate genes which must first be induced in cells, that is, which are not continuously being transcribed, for example transient genes, such as genes responsible for programmed cell death, cell cycle genes, DNA repair genes and differentiation specific genes, an additional process is necessary, in order conclusively to identify the transient cellular promotor captured in the gene trap, for instance through a durable signal independent of the promotor activity. Approximately 50% of the genes which are switched off in ES cell lines following infection/electroporation by gene-trapping vectors, manifest recessive phenotypes in mice (Friedrich and Soriano, 1991; Skarnes et al., 1992; von Melchner et al., 1992). This frequency is ten times greater than that observed following accidental insertion of retroviruses or microinjection of DNA (Gridley et al., 1987; Jaenisch et al., 1985). Due to this high efficiency of gene inactivation it appears sensible to isolate cell lines which display integration in most of the genes expressed ($2-4\times10^4$). It is not very practical, however, to transfer all mutations into the original line; furthermore many mutations result in genes of more limited significance. Consequently it would be desirable to exchange mutagenized ES cell clones for mutations relevant to important biological processes or genes.

With reference to this, those strategies are especially suitable which involve the preliminary selection of ES cell clones from interesting in vitro mutations, and for this employ a reporter gene to identify mutations e.g. in differentiation-specific genes. Although cultivated ES cells might have expressed genes which are not expressed in vivo, in 12 cases fusion genes were found which were expressed in ES cells as well as in embryos (De Gregory et al., 1994; Reddy et al., 1992). It further appears to be the case that a change in the expression of fusion genes during differentiation in vitro very closely predicts the change in expression during in vivo development (Reddy et al., 1992). This is in general agreement with earlier observations, in which in vitro-regulated genes were also strictly regulated in vivo (Muthuchamy et al., 1993; Rappotee et al., 1988; Rogers et al., 1991; Scholer et al., 1990; Sharpe et al., 1990).

SUMMARY OF THE INVENTION

The invention under consideration concerns a gene-trapping construct containing a first reporter gene, which after activation can activate a second reporter gene, and the use of this gene-trapping construct for identification and/or isolation of genes, especially transiently expressed (transient) genes.

In addition the invention under consideration concerns a cell, preferably a mammalian cell, which contains the above-mentioned gene-trapping construct. Besides this the invention under consideration concerns the use of this mammalian cell for identification and/or isolation of genes, particularly transient genes. Furthermore the invention concerns a vector containing the abovementioned gene-trapping construct, as well as a kit, containing at least the abovementioned gene-trapping construct or the abovementioned vector, for the identification and/or isolation of genes, particularly transient genes.

In conclusion the invention under consideration concerns a process for the identification and/or isolation of genes, particularly transient genes.

It was therefore intended according to the invention under consideration to prepare a gene-trapping construct which made possible the isolation and identification of genes, especially transient genes, in a particularly advantageous way. A further purpose in respect to the invention under consideration was to provide a cell as well as a vector which maintained this gene-trapping construct, together with a kit for the identification and/or isolation of genes.

In conclusion, it was an intention according to the invention under consideration to present a process for the identification and/or isolation of genes, especially transient genes.

BRIEF DESCRIPTION OF THE DRAWINGS

The appended figures should explain the invention under discussion:

FIGS. 1A and 1B show the process relating to the invention in a schematic representation of two favoured operational forms.

(A) Activation mechanism of the endogenous IL-3 secretion in FLOXIL-3 cells after IL-3 withdrawal. Integration of a U3-Cre gene trap into an originally unexpressed apoptosis gene is transiently activated by IL-3 withdrawal (left). Through site-specific recombination of the reporter plasmid ppgklxtkneoIL3 the tkneo gene is eliminated and the IL-3 gene is placed immediately downstream of the pgk promotor. This results in sustained IL-3 synthesis which continues even after switching off of the gene captured in the gene trap.

(B) Activation mechanism of the lacZ gene during differentiation of -pIn13-totipotent embryonic stem cells. A U3-Cre gene trap integration into an originally unexpressed differentiation gene is transiently activated during the differentiation. Through site-specific recombination of the reporter plasmid ppgklxneoLacZ the LacZ gene is placed immediately downstream of the pgk promotor. This results in sustained synthesis of beta-galactosidase, which continues even after switching off of the gene captured in the gene trap.

Figure 1A:
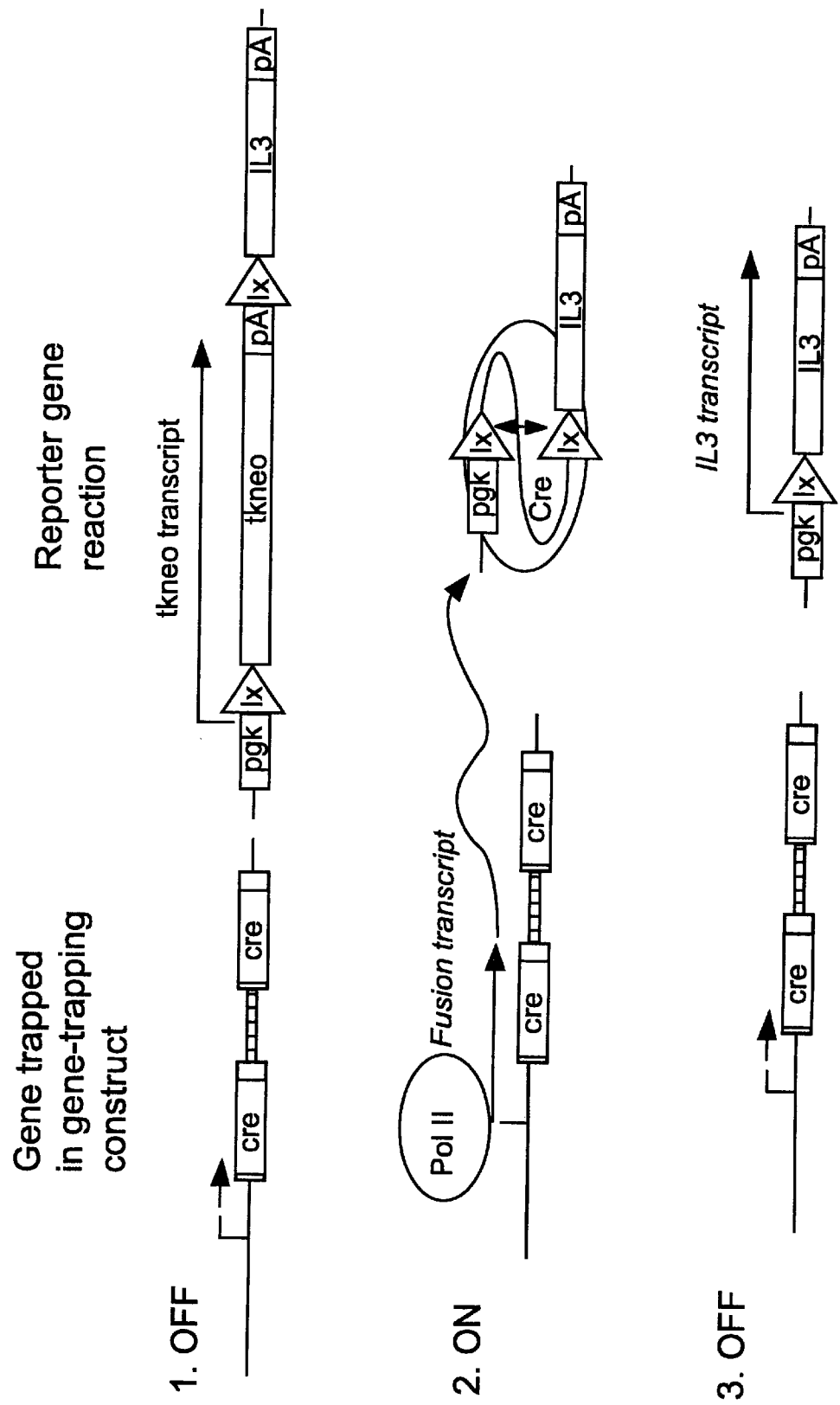
Figure 2:
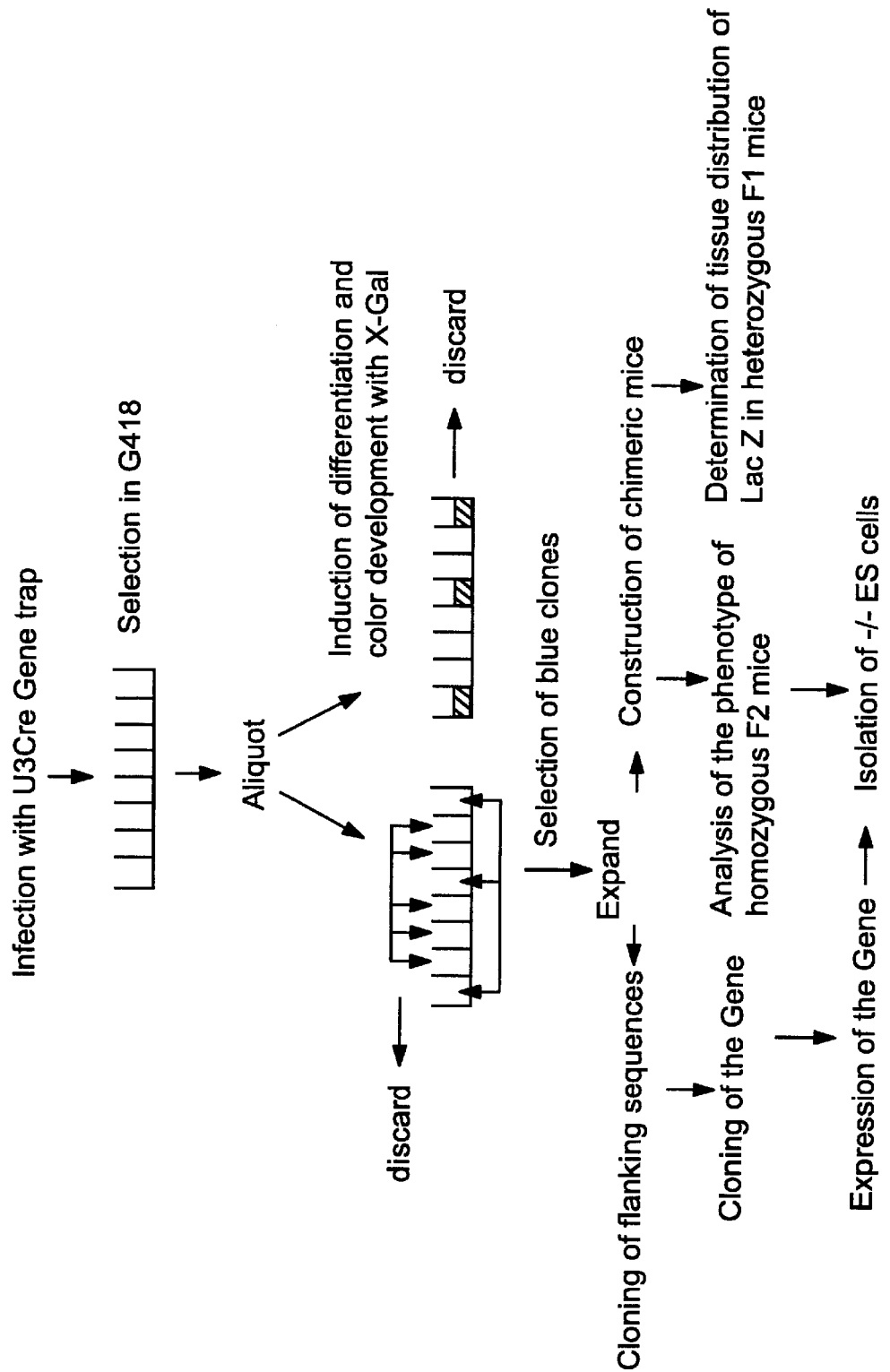

FIG. 2 shows a schematic overview of a process for the isolation and analysing of inducible differentiation genes from embryonic stem cells.

Figure 3:
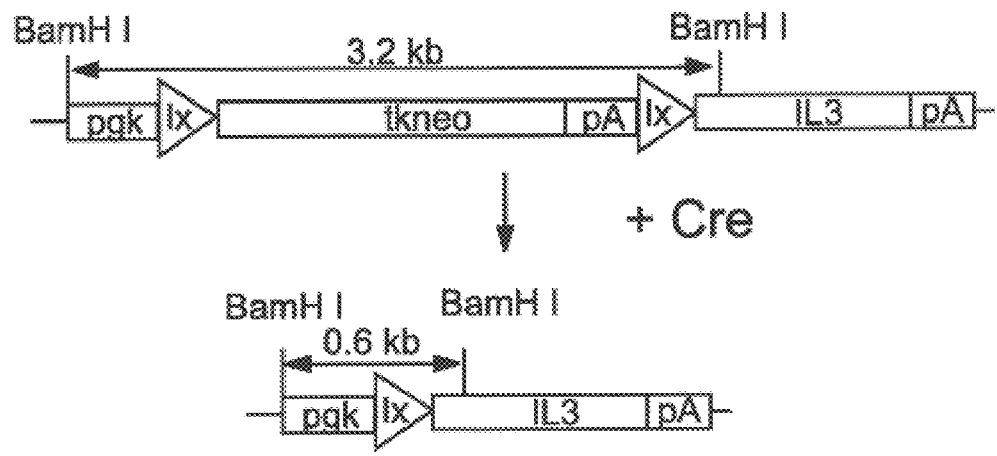
Figure 3:
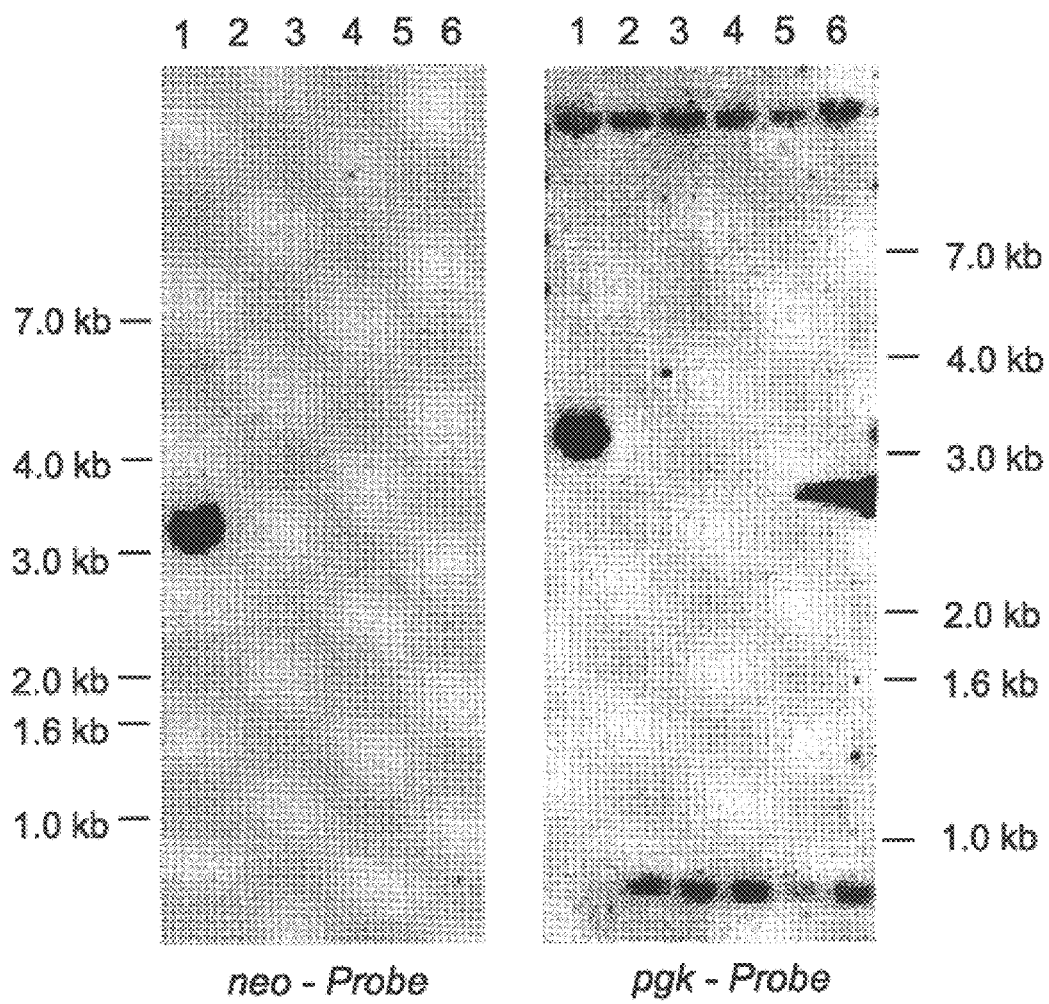

FIGS. 3A and 3B show the Cre/loxP-mediated recombination of the ppgklxtkneoIL3 plasmid in FLOXIL-3 cells with U3-Cre-gene trap integrations in expressed genes.

(A) Structure of ppgklxtkneIL3 before and after recombination.

(B) Southern-Blot analysis of autonomous and parental FLOXIL-3 cells. Genomic DNAs were cut with BamHI, fractionated in agarose gels and transferred on to nylon membranes. Hybridization followed with $^{32}$P-labelled neo- (left) or pgk-specific probes. Lane 1: parental FLOXIL-3 cells; Lanes 2–6: autonomous clones 1–5. Molecular weights are expressed with the help of a 1-kb BRL scale.

Figure 4:
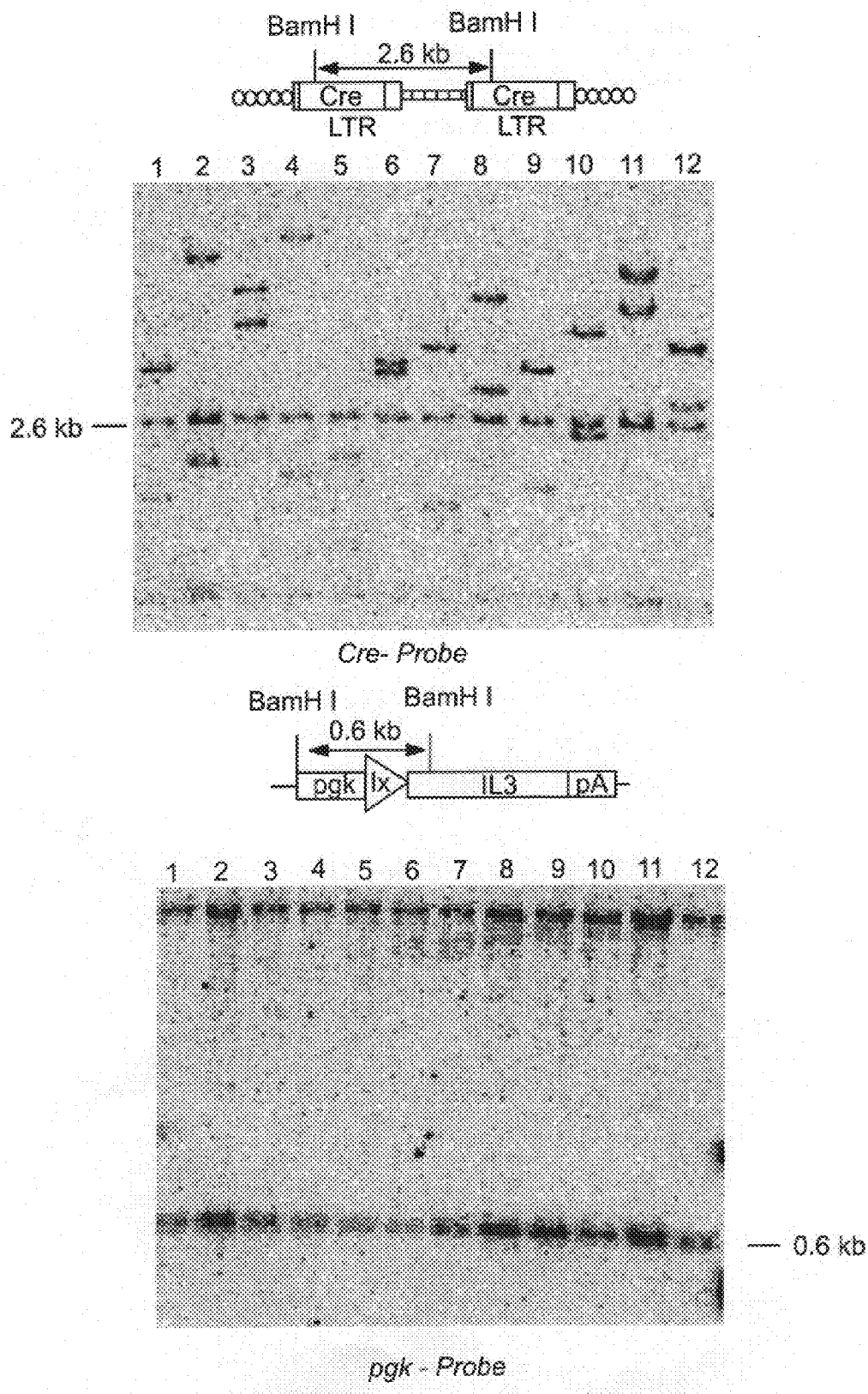

FIG. 4 shows U3-Cre gene trap integrations and site-specific recombination in autonomous clones isolated after withdrawal of IL-3. (Above) Expected structure of U3-Cre proviruses (left) and the recombined reporter plasmid (right). (Below) Southern-Blot analysis of clones isolated following IL-3 withdrawal from the U3-Cre/FloxIL-3 integration bank. The genomic DNA of individual clones was cut with BamHI and treated as in the text of FIG. 3. Hybridization followed with $^{32}$P-labelled Cre- (left) or pgk- (right) specific probes. Lane 1, 26-11-1; lane 2, 26-11-3; lane 3, 26-11-4; lane 4, 26-11-5; lane 5, 26-11-6; lane 6, 26-11-7; lane 7, 26-11-8; lane 8, 26-12-1; lane 9, 26-12-2; lane 10, 26-12-3; lane 11, 26-12-4; lane 12, 2612-5. The probes illustrated are representative of the whole integration bank.

Figure 5:
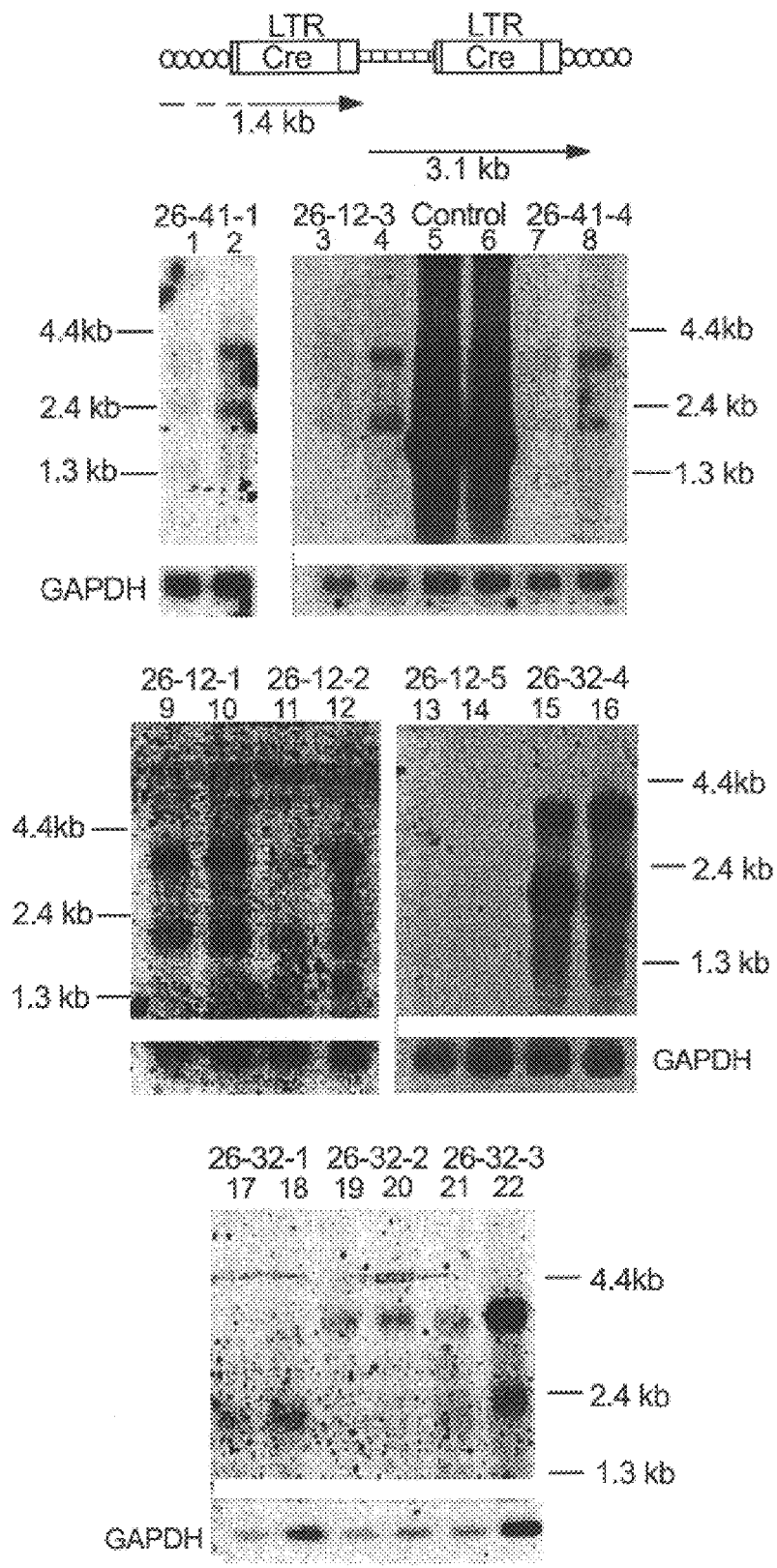

FIG. 5 shows an investigation of the cell-provirus fusion transcript. (Above) Transcript expected from U3-Cre gene-trap integration in expressed genes. (Below) Northern-Blot analysis of cell-provirus fusion transcripts before and after serum withdrawal. Polyadenylated RNA (5 micrograms) was fractionated in formaldehyde-agarose gels and transferred on to nylon membranes. Hybridization followed with $^{32}$P-labelled Cre- or GAPDH-specific probes. Odd numbers stand for RNAs, even numbers RNAs after 16-hour serum withdrawal. Lanes 5 and 6 contain RNA from a clone with a constitutively expressed U3-Cre integration.

Figure 6:
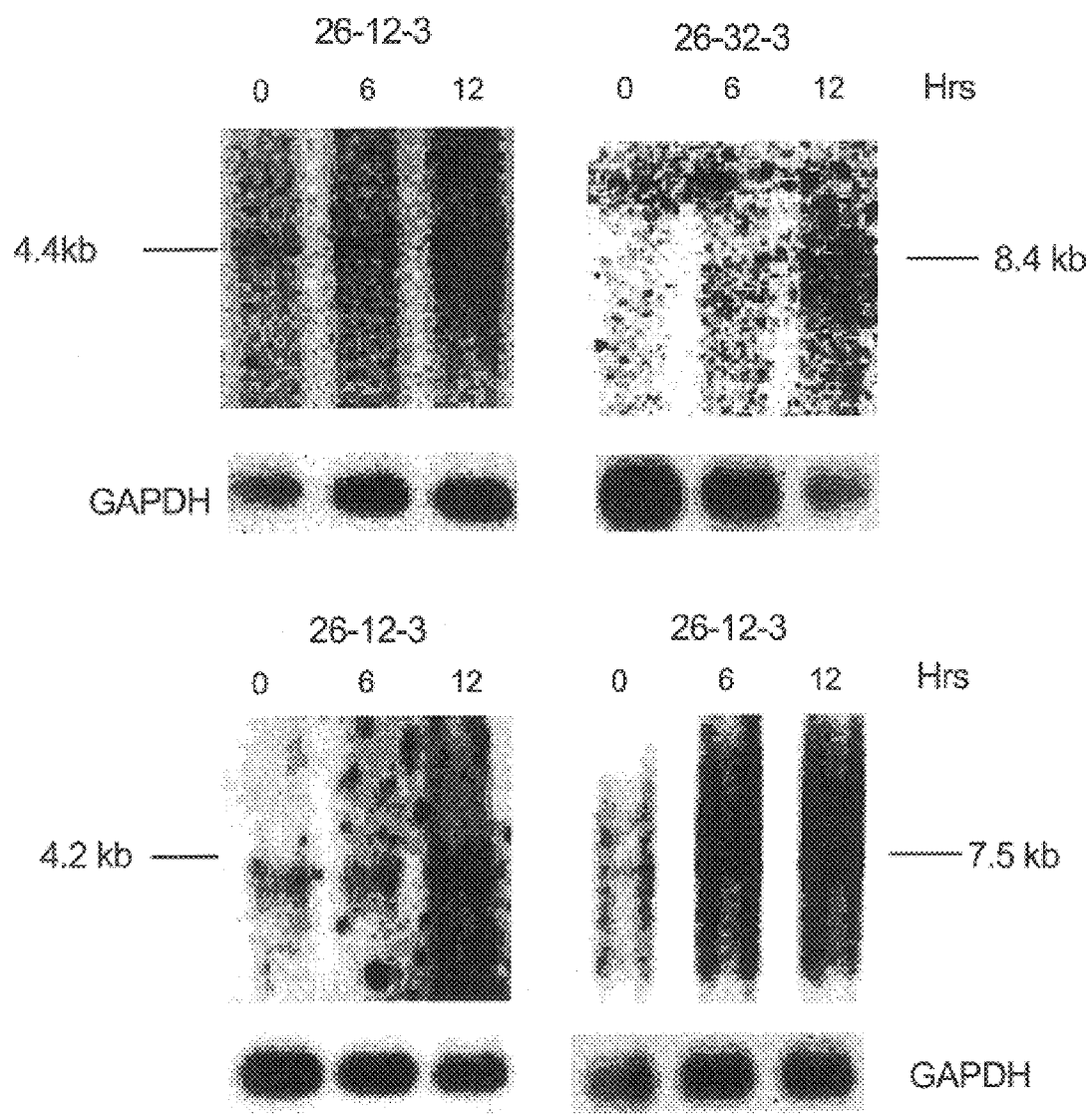

FIG. 6 shows an investigation of cellular transcripts following IL-3 withdrawal. Polyadenylated RNA (5 micrograms per lane) was derived from FDCP-1 cells deprived of IL-3 for 0, 6 and 12 hours. Northern-Blots were constructed as in the text of FIG. 5 and hybridized with $^{32}$P-labelled 5' provirus-flanking sequences or GAPDH.

Figure 7A:
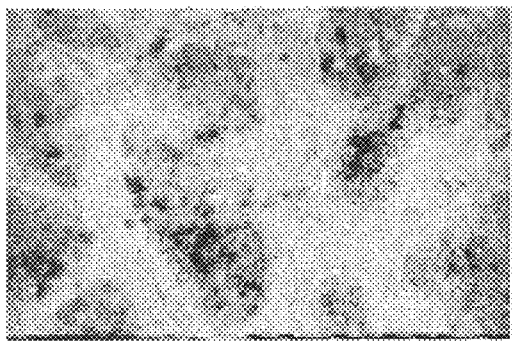
Figure 7A:
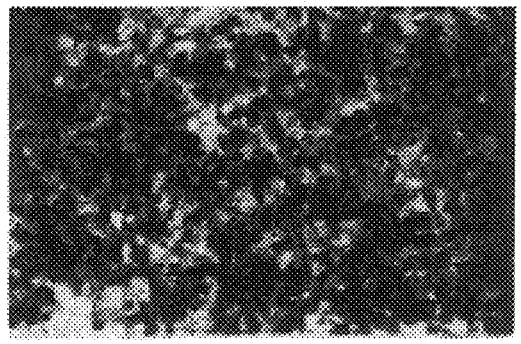
Figure 7A:
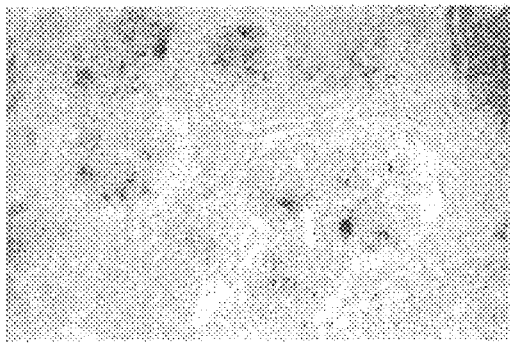
Figure 7A:
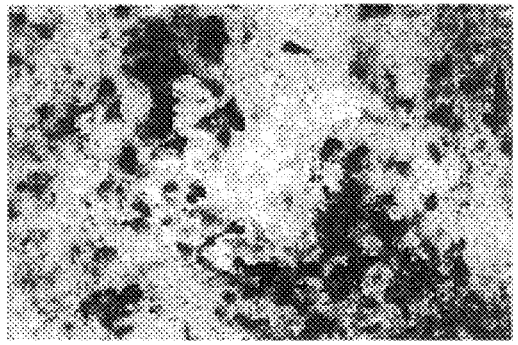
Figure 7A:
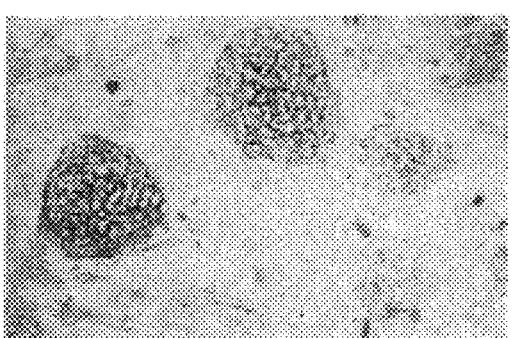
Figure 7A:
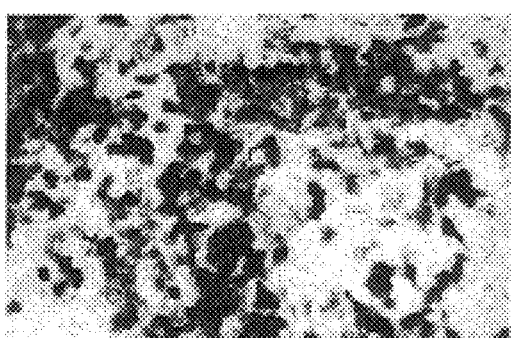
Figure 7B:
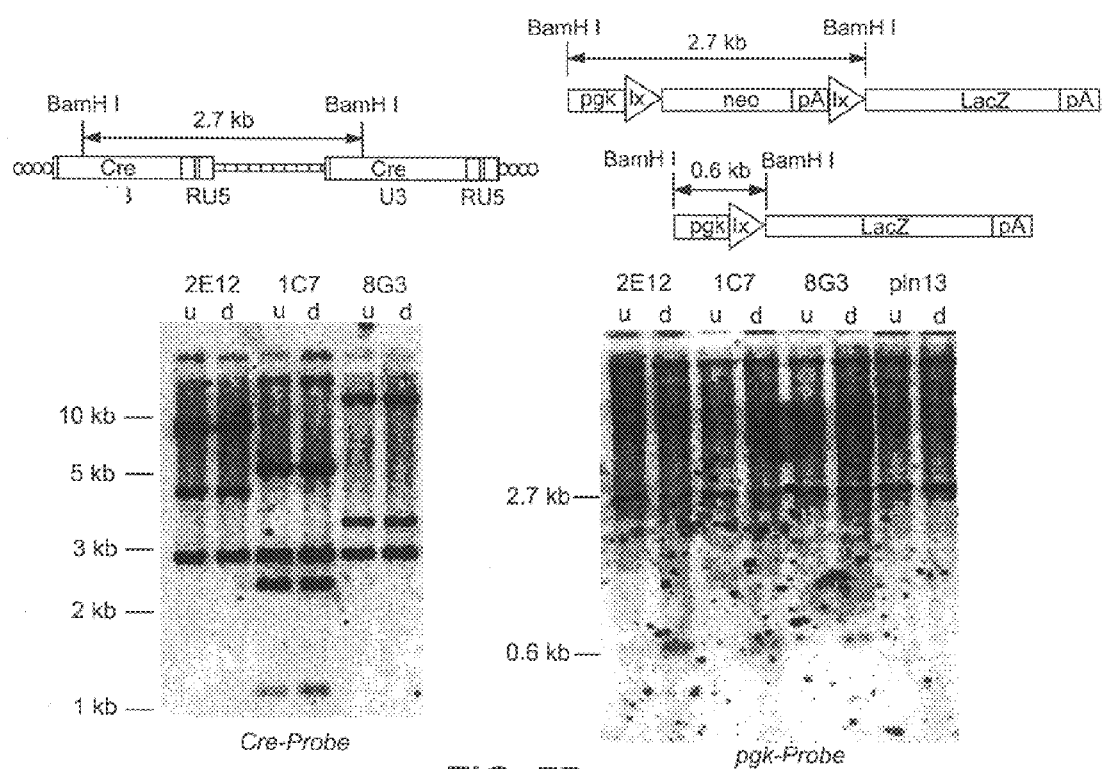

FIGS. 7A and 7B show the differentiation-regulated U3-Cre gene trap integrations into embryonic stem cells. 960 pools each of 150 cells were infected with the U3-Cre virus and selected in G418. Differentiation induction followed over 4 days.

(A) X-Gal staining before (left) and after (right) induction of differentiation.

(B) Southern-Blot analysis of the regulated clones. The genomic DNA was cut with BamHI and treated as in the text of FIG. 3. Hybridization followed with $^{32}$P-labelled Cre— (left) and pgk—(right) specific probes.

u=undifferentiated, d=differentiated.

DETAILED DESCRIPTION OF THE INVENTION

The preferred types of operation with respect to the invention under consideration are presented in the claims below.

A "reporter gene" here signifies a nucleic acid sequence which gives rise on transcription to a recognizable signal such as for example a protein product. The "first" reporter gene is regulated through cellular transcription signals in whose neighbourhood it is integrated. Once the first reporter gene is activated, the first reporter gene product leads to activation of the "second" reporter gene, in which this second activation is permanent, that is, independent of the transcriptional activity of the DNA region controlling the first reporter gene. The second reporter gene codes for a demonstrable gene product, such as for example an enzyme, demonstrable by a colour reaction, or a growth factor, which can then be selected for. The result of the combination of first and second reporter genes is that even an only transiently expressed promotor can be indicated by means of a permanent signal, the second reporter gene product. The first and second reporter genes may exist in a common construct, or they may be available in various devices present in various places in the cell. The gene-trapping construct according to the invention is consequently here in principle a combination of a conventional gene-trapping construct, such as for example that described in U.S. Pat. No. 5,364,783, corresponding to the first reporter gene construct, and a further device which can provide a permanent product independently of the promotor activity, in the present instance the second reporter gene construct.

According to the invention under consideration, a gene-trapping construct is presented containing a first reporter gene which following activation can activate a second reporter gene. The first reporter gene preferably codes for a recombinase, such that this recombinase is in particular preferentially Cre or Flp.

In a favoured operational form the second reporter gene may code for a protein factor, in a further favoured operational form the second reporter gene codes for IL-3 and in a particularly favoured further operational form for E. coli beta-galactosidase (lacZ). The second reporter gene is preferably activated by deletion by the recombinase of a DNA fragment situated next to the second reporter gene, which thereby places the second reporter gene immediately downstream of a promotor permanently under its control.

The deleted DNA fragment may preferentially be an antibiotic-resistance gene, by means of which the deleted DNA fragment codes in aparticularly favoured operational form for thymidine kinase-neomycin phosphotransferase fusion protein, and in a further particularly favoured operational form codes for a neomycin phosphotransferase.

The promotor before which the second reporter gene is placed is preferably the phosphoglycerate kinase promotor.

In a favoured operational form the deleted DNA fragment is flanked by sequences, which may for example be loxP or frt, targeted by the recombinase. A possibility also exists that the target sequences may be located in the U3 and/or the U5 region. The gene-trapping construct described above can be used for identification and/or isolation of genes, particularly transient genes. Included under this particularly is the isolation and/or identification of genes responsible for programmed cell death, cell cycle genes, DNA repair genes and differentiation-specific genes.

The invention under consideration furthermore provides for a cell, preferably a mammalian cell, containing a gene-trapping construct such as that described above.

In a favoured operational form the mammalian cell is dependent on IL-3 and contains a genetrapping construct in which the first reporter gene codes for Cre recombinase, whereby the Cre recombinase can delete a DNA fragment situated before the second reporter gene, where the deleted fragment codes for a thymidine kinase-neomycin phosphotransferase fusion protein and is flanked by loxP target sequences, and where the second reporter gene codes for IL-3 and following deletion of the thymidine kinase-neomycin phosphotransferase fusion protein gene comes to lie immediately downstream of the phosphoglycerate kinase promotor.

It is especially preferred that the mammalian cell is a growth factor-dependent haematopoietic precursor cell (e.g. FDCP1) or a totipotent embryonic stem cell.

According to the invention under consideration the mammalian cell can be used for identification and/or isolation of genes, especially transient genes, by which means particularly identification and/or isolation of the genes responsible for programmed cell death, of cell cycle genes, DNA repair genes and differentiation-specific genes is favoured.

Furthermore the invention under consideration provides for a vector containing the gene-trapping construct described above.

In addition a kit for the identification and/or isolation of genes, particularly transient genes, is proposed, containing at least one gene-trapping construct such as is described above.

Preferably the kit contains two constructs, by which the first construct contains the first reporter gene and the second construct the second reporter gene.

The kit may also contain a vector such as described above.

In conclusion, the invention under consideration provides a process for the identification and isolation of genes, especially transient genes, which contains the following steps:
  Installation of a gene-trapping construct as described above, in a suitable cell;
  Selection of cells in which the first reporter gene is incorporated in a gene, preferably an inactive gene;
  Activation of the first reporter gene, preferably by initiation of transcription of the inactive gene, in consequence of which the second reporter gene is activated;
  Identification and/or isolation of the gene in which the first reporter gene is incorporated.

In a favoured operational form the process described above is characterized thereby, that
  a gene-trapping construct such as described above contains as first reporter gene the Cre recombinase gene, and that the Cre recombinase deletes a thymidine kinase-neomycin phosphotransferase gene situated upstream of the second reporter gene, through which the second reporter gene, which codes for IL-3, comes under the control of a phosphoglycerate kinase promotor,
  the gene-trapping construct is inserted into an IL-3-dependent FDCP-1 cell,
  through culture in neomycin- (e.g. G 418-)containing medium cells are selected for which do not produce Cre recombinase,
  these selected cells are cultivated in IL-3-free medium so that the genes responsible for programmed cell death are activated,
  that the surviving cells are selected out and
  the genes responsible for programmed cell death are isolated by the customary procedures.

In a further favoured operational form the process is thereby characterized, that
  a gene-trapping construct, as described above, contains the Cre recombinase gene as first reporter gene, and that the Cre recombinase deletes a neomycin phosphotransferase gene situated upstream of the second reporter gene, through which the second reporter gene, which codes for lacZ, comes under the control of a phosphoglycerate kinase promotor,
  the gene-trapping construct is inserted into a totipotent embryonic stem cell,
  through cultivation on G418 cells are selected for which do not produce Cre recombinase,
  these selective cells are induced to differentiate, so that differentiation-specific genes are activated,
  these cells are isolated,
  these cells are introduced into the germ line of a mammal and are responsible there for the shaping of tissues, and
  the differentiation-specific genes are isolated by the customary procedures.

The abovementioned process for the isolation of the genes responsible for programmed cell death is for this reason especially appropriate, since through permanent replacement of selection markers by a gene trap expressing Cre recombinase, they are converted through activation in essentially dying cells of the endogenous cytokine production into multiplying cells. This permits selection for integration into genes which are active during the programmed cell death. Expression of the selection marker, for instance IL-3, is disassociated from the expression of the localized gene (in the gene trap) by which the recombinase brings the selection marker behind the phosphoglycerate kinase promoter. This is especially important as it is improbable that cells should go on expressing the genes responsible for programmed cell death. Finally, the process according to the invention under discussion is not confined to strongly expressed genes, and the gene representation is very much more uniform than for example in cDNA cloning. Furthermore the use of gene traps for isolation and/or identification, unlike differential RT-PCR amplification, is well reproducible, avoids redundancy and even enables quantification. In conclusion, the gene trap proviruses are regularly located in or near the 5' exon and have the same transcriptional orientation relating to the gene, and this clearly facilitates cloning.

In any case characterization of the cellular transcripts induced by IL-3 withdrawal makes possible deeper insights into the complex molecular changes taking place during programmed cell death.

In a further favoured operational form a totipotent cell, which in itself can develop into an entire organism, contains a construct whereby the first reporter gene codes for a Cre recombinase which can delete a fragment situated before the second reporter gene, whereby the deleted fragment codes for neo and is flanked by loxP target sequences, and the second reporter gene codes forlacZ which following deletion of neo comes to lie immediately downstream of pgk.

Particulars of this are to be found in the Examples.

In the following the invention will be described in detail with the help of examples; the examples will not however be limited to the scope of the invention.

EXAMPLES

Example 1
Construction of a Reporter Plasmid

Most of the components of the reporter plasmid ppgklxtkneoIL-3 (phosphoglycerate transferase promotor, loxP target sequence, thymidine kinase-neomycin phosphotransferase fusion protein, IL3 gene) were put together in p-BluescriptII-KS as follows:

The sequences for the target sequence loxP were derived from pGEM30. A loxP site was inserted at first into the Bluescript Polylinker as an EcoRl/Psti fragment. Then pgk (phosphoglycerate kinase promotor, obtained from ppgkCAT) was ligated to the XbaI/BamHI recombination site of the polylinker and the thymidine kinase-neomycin phosphotransferase fusion gene was cloned in the EcoRV recombination site situated downstream. The IL-3 gene (as cDNA of mice, from pc-MultiCSF) was first subcloned from pGEM30 in the EcoRI site of the polylinker flanking the loxP target sequence, then next the plasmid was cut with ClaI/SalI and the endfilled ends were again ligated to remove an additional EcoRI site. IL-3-loxP was then recovered from pGEM30 as an SalI/XhoI fragment and cloned in the Bluescript Polylinker. A copy of the bovine growth hormone polyadenylation sequence (bpa) as XbaI/AvaI fragment was cloned with blunt ends in the ClaI site downstream of tkneo. In order to obtain ppgklxtkneoIL-3 a XhoI fragment containing the assembled sequences was cloned in pSBC2 upstream of an SV-40 polyadenylation site. Since this original construct still enabled translation of IL-3 from the dicistronic tkneo-IL-3 transcript, a second copy of bpa with blunt ends was cloned in the SalI site of pSBCII in order to obtain the definitive ppgklxtkneoIL-3 reporter plasmid.

Example 2
Construction of an FDCP1 Reporter Cell Line Expressing Two Selectable Reporter Genes Flanked by loxP Recombination Targets The FDCP1 haemopoietic precursor cells used are strictly dependent on IL-3 for their growth and initiate programmed cell death if this growth factor is withdrawn from the medium.

The FDCP1 cells were cultivated at concentrations of $2 \times 10^5$ cells per ml in Dulbeccos modified Eagle's medium (DMEM: Gibco) supplemented with 10% v/v foetal calf serum (High Clone Laboratories, Utah, USA) and 10 ng/ml recombinant mouse IL-3 (Sandoz). The agar cultures were a mixture of equal volumes of double-strength DMEM supplemented with 40% (v/v) foetal calf serum (Hyclone) and 0.6% (w/v) Bactoagar (Difco) in twice-distilled water. A few cultures contained 5 muM ganciclovir (Syndex).

In order to obtain a cell line which is transformed by Cre recombinase into a factor-independent cell, FDCP1 cells were electroporated with the reporter plasmid ppgklxtkneoIL-3. The electroporation was carried out using a BioRad Gene Pulser (BioRad) following the instructions of the manufacturer. The recombinants were isolated in agar culture containing 0.6 mg/ml G418. After 10 days the developing clones were isolated and amplified in suspension cultures as described above. The ppgklxtkneoIL-3 (FIG. 3A) consists of two selectable reporter genes arranged one after the other, which are transcribt from a pgk (phosphoglycerate kinase) promotor. The gene at the 5' end codes for an HSV2 thymidine kinase (Tk) neomycin phosphotransferase (neo) fusion protein and is flanked by two loxP recombination targets. The 3' end of the gene codes for mouse IL-3 and terminates in an SV40 polyadenylation sequence. To suppress the IL-3 translation of dicistronic transcripts, two consecutively arranged copies of the polyadenylation sequence of bovine growth hormone (bpa) were inserted downstream from tkneo. In this way one could assume that even cells which expressed ppgklxtkneoIL-3 were still always IL-3 dependent. Since the Cre recombinase typically excises those sequences that are flanked by direct repetitions of lox-P, it was assumed that expression of Cre deleted the tkneo gene and thereby placed the IL-3 gene downstream of the pgk promotor. As a result the cells would lose their neomycin resistance and acquire factor independence through synthesis of IL-3.

Stable FDCP-1 transformants were selected in G418 and five clonal cell lines were isolated from the agar cultures. A cell line expressing a single-copy plasmid and in addition identified as FLOXIL 3 was selected for further analysis.

It was first established whether the FLOXIL-3 cells were still dependent for their growth on IL-3, by plating out $5 \times 10^7$ cells at a concentration of $2 \times 10^5$ per ml in half-set agar cultures without IL-3. Since no colonies developed within 10 days, it was assumed that neither limited IL-3 translation nor spontaneous recombination had occurred inside these cells.

Further to confirm this, FLOXIL-3 and parental FDCP-1 cells were pre-incubated in agar cultures without IL-3 for up to 24 hours and finally rescued by giving IL-3. Both cell types initiated programmed cell death with similar kinetics, which indicated that the expression of ppgklxtkneoIL-3 did not alter the cellular response to the factor withdrawal. Moreover most of the cells survived for more than 12 hours without IL-3 and so left enough time for the expression of the sequences transduced by the gene trap.

Example 3
Construction of a Gene Trap which Expresses Cre Recombinase (U3-Cre) and Renders FLOXIL-3 Cells Factor-independent A U3-Cre gene-trap vector was derived from the pGgU3Neo(en-) vector based on MoMuLV, by means of which the neo gene in the U3 region was replaced with the sequence coding for Cre derived from pMCCre. The plasmid was transfected into helper cells, and the remainder of the cell line, which produced recombinant viruses in high titre, was used for infecting FLOXIL-3 cells. As already indicated earlier, the virus replication and LTR-mediated duplication of sequences inserted into U3 places precisely 30 nucleotides downstream of the flanking cellular DNA. This enables their expression through integrations into transcribed genes. It was expected from this that FLOXIL-3 cells with U3-Cre integrations in expressed genes would be transformed into factor-independent cells. In order to select for this occurrence, virus-infected FLOXIL-3 cells were plated out in agar cultures without IL-3. Many autonomously growing colonies were obtained and amplified in suspension cultures. As was to be expected from the expression of a recombinant reporter plasmid, all the clones lost their G418 resistance and grew without IL-3.

In order to verify the recombination, genome DNAs from five autonomous clones were digested with BamHI and analysed by Southern blotting. Since BamHI divides inside the 5' ends of pgk and IL-3, recombinant FLOXIL-3 cells do not replicate an internal fragment of 3.2 kb which hybridizes both with pgk- and with neo-specific probes (FIG. 3A). Since this fragment contains all the sequences which are flanked by loxP, including tkneo, a deletion should be associated with a reduction in size of 2.6 kb. In fact all clones produced a 0.6 kb restriction fragment which did not hybridize with neo, which indicated that recombination had taken place (FIG. 3B).

Furthermore, when analysed by Northern blotting all the clones expressed cell provirus transcripts, which indicated that the Cre recombinase of active cellular promotors was being expressed.

In this way FLOXIL-3 cells are obtained containing a gene-trapping construct which enables such genes as are responsible for programmed cell death to be isolated and identified.

Example 4
Construction of a U3-Cre/FLOXIL-3 Integration Bank and Isolation of Transiently Expressed Gene Sequences An integration bank consisting of $2 \times 10^6$ independent proviral integrations was constructed by infection of FLOXIL-3 cells with U3-Cre retroviruses. The infected cells were first preselected in G418 in order to eliminate complete integrations into expressed genes. FIG. 4 shows that this goal was attained following 16 days' selection. Following plating out of a basic sample of the integration bank in agar culture without IL-3, altogether 110 autonomous clones could be isolated and amplified. Southern blot investigations have shown that all the clones displayed provirus, 4 integration and without exception contained recombinant reporter plasmids (FIG. 4).

Northern blot investigations with mRNA from 11 independent autonomous clones show that in 9 clones cell-provirus fusion transcripts were either very weakly expressed or not at all (FIG. 5, lanes 1, 3, 7, 9, 11, 13, 17, 19, 21). This means that the Cre recombinase was only transiently expressed sufficiently to cause recombination of the reporter plasmid. In addition more than 50% of these fusion transcripts were inducible by serum withdrawal, which indicates, that the genes intercepted by the gene trap are associated with arrest of an apoptotic programme or of growth (FIG. 5).

Finally the 5'-provirus-flanking sequences cloned by known processes (von Melchner et al., 1992) were hybridized with the mRNA of wild-type FDCP-1 cells on Northern blots. The majority of the probes investigated hybridized with IL-3-induced cellular transcripts (FIG. 6). Whether these genes control the apoptosis directly or are part of other mechanisms which are activated as a result of the programmed cell death, still has to be established. In any case characterization of the cellular transcripts induced by the IL-3 withdrawal facilitates further insights into the complex molecular changes which emerge during programmed cell death. The further precise identification and isolation of the discovered genes can be carried out by customary processes, such as for instance 3'RACE or the restoration of a gene library and cloning and sequencing of the genes discovered.

Example 5
Construction of an ES Reporter Cell Line

In order to obtain an ES cell line suitable for a permanent selectable reporter exchange through Cre recombinase, D3 cells were electroporated with the reporter construct ppgklxneolacZ in which two reporter genes arranged one after the other were transcribed by a mouse phosphoglycerate kinase promotor. The reporter construct ppgklxneolacZ consists of the phosphoglycerate kinase promotor, the loxP target sequences, the neomycin phosphotransferase gene and a gene for LacZ. Its construction followed the pattern described above for construction of the reporter plasmid ppgklxtkneoIL-3.

The 5' gene codes for neomycin phosphotransferase and is flanked by two loxP recombination targets in identical orientation. The 3' gene codes for beta-galactosidase and ends in an SV40 polyadenylation sequence. In order to suppress genomic transcripts ending in SV40-PolyA and in this way also to suppress the translation of LacZ, two consecutively positioned copies of the bovine growth hormone polyadenylation sequence (bpa) are inserted downstream of the neomycin phosphotransferase. Cells expressing ppgklxneolacZ should accordingly display a phenotype resistant to neomycin phosphotransferase and negative for LacZ. In the case of Cre expression, however, the neo gene would be excised from the recombinase and the sequence coding for LacZ placed immediately downstream of the pgk promotor. As a result the cells which express the recombined reporter plasmid lose their neomycin resistance and stain positive with X-Gal (LacZ+). Various ES cell lines expressing ppgklxneolacZ were isolated in G418 and tested individually on a background of X-Gal staining. Four of 10 cell lines did not stain regularly with X-Gal even after long periods of culture. If one induced these cell lines to differentiate in cultures containing no LIF (Leukaemia Inhibiting Factor) or nutrient layers, LacZ cells still stained negative, which indicated that the LacZ phenotype is stable. A cell line expressing a single copy of ppgklxneolacZ was selected for further analysis. In the following it is named pIn13.

In order to establish whether the Cre recombinase converted the LacZ of pIn13 into LacZ+, the cells were transfected with the Cre-expressing plasmid pMC-Cre Unselected colonies were picked after 10 days and aliquots stained with X-Gal. Genomic DNA extracted from various LacZ+ cells was cut with BamHI and analysed by Southern blotting. In every case the LacZ phenotype was associated with a 2 kb deletion, which indicated that the reporter plasmid was subject to site-specific recombination.

Example 6
Expression of Beta-galactosidase in pIn13 Cells through U3-Cre Integration $5 \times 10^4$ pIn13 cells were infected at MOI=1 with U3-Cre virus constructed as described above. After incubation for 72 hours the cells were divided into 480 pools and seeded out in microtitre plates. After 48 hours aliquots were stained with X-Gal in order to detect integrations into active cells. Out of 20 pools containing LacZ+ cells three were seeded out at clonal density. Four positive clones were selectively isolated and analysed by Southern blotting. All clones contained 1–2 proviruses which agreed with an MOI=1 and contained recombined reporter plasmids. Every clone in addition expressed cell-provirus fusion transcripts whose size in accordance with expectations varied around 100 to 500 nt.

In this way U3-Cre gene trap retroviruses effectively mediate site-specific recombinations on account of their integration into expressed genes.

Example 7
Isolation of Clones with Inducible U3-Cre-provirus Integration

In order to establish whether the U3-Cre/loxP strategy is suitable for isolating genes which owing to differentiation are inducible, $1.5 \times 10^5$ pIn13 cells were seeded out in the cups of 10 microtitre plates at concentrations of 150 cells per cup and infected with U3-Cre virus at about MOI=1. In order to eliminate integration into active genes, cells were selected on G418 for 5 days. Then in the absence of either LIF (Leukaemia Inhibitory Factor) or MEF (Mouse Embryonic Fibroblasts) aliquots of each cup were induced to differentiate and stained with X-Gal. Forty-four out of 960 cups stained positive by this test. Following a further test 9 pools were LacZ+ in both presence and absence of LIF and MEF, while 35 pools changed to LacZ+ only following differentiation, which indicated that U3-Cre integration had occurred in the induced genes.

FIG. 7 shows as an example three isolated clones with U3-Cre-provirus integrations into differentiation-specific genes. The inducibility of the genes was attested by the phenotypic change from LacZ(−) (FIG. 7A, undifferentiated cells, above left) to LacZ(+) (FIG. 7A, differentiated cells, above right). The Southern Blots indicate that this change is based on site-specific recombination of the reporter plasmid, caused by the U3-Cre-provirus integration into inducible differentiation genes (FIG. 7B).

In FIG. 2 is shown an overview of an isolation of this kind. In the first step come infection with U3Cre gene trap vector and selection on G418. The colonies obtained are divided into aliquots, induced to differentiate and stained with X-Gal. Only the stained clones are selected further, amplified and used in the construction of chimaeric mice. These mice may on the other hand be used to determine the LacZ distribution in the tissue, or to determine the phenotype of F2 mice and to isolate −/−ES- cells.

The corresponding cellular genes can be cloned from the known gene-trap sequences by conventional means.

In this manner the gene trapping construct according to the invention under consideration makes it possible to isolate and/or identify genes, in particular genes only transiently expressed.

Bibliography

Coffin, J. M., Stoye, J. P., and Frankel, W. N. (1989). Genetics of endogenous muririe leukemia viruses. Ann. N Y Acad. Sci. 567, 39–49.

Goff, S. P. (1990). Integration of retroviral DNA into the genome of the infected cell. Cancer Cells, 172–178.

Gridley, T., Soriano, O., and Jaenisch, R. (1987). Insertional mutagenesis in mice. Trends Genet. 3, 162–166.

Hill, D. H. P., and Wurst, W. (1993). Mutagenic strategies to dissect mammalian development. Curr. Topics. Dev. Biol. 28, 181–206.

Hill, D. H. P., and Wurst, W. (1993). Screening for pattern formation in mouse using gene trap technology. Methods Enzym. 255, 663–681.

Muthucharny, M., Pajak, L., Howles, P., Doetschman, T., and Wieczorek, D. (1993). Developmental analysis of tropomyosin gene expression in embryonic stem cells and mouse embryos. Mol. Cell. Biol. 13, 3311–3323.

Rappolee, D. A., Brenner, C. A., Schultz, R., Mark, D., and Werb, Z. (1988). developmental expression of PDGF, TGF-a and TGF b in preimplantation mouse embryos. Science 247, 1823–1825.

Reddy, S., Rayburn, H., von Melchner, H., and Ruley, H. E. (1992). Fluorescence activated sorting of totipotent embryonic stem cells expressing developmentally regulated lacZ fusion genes. Proc. Natl. Acad. Sci. USA 89, 6721–6725.

Rogers, M. B., Hosler, B. A., and Gudas, L. J. (1991). Specific expression of a retinoid acid-regulated, zinc-finger gene, Rex-1, in preimplanation embryos, trophoblast and spermatocytes. Development 113, 815–824.

Sandmeyer, S. B., Hansen, L. J., and Chalker., D. L. (1990). Integration specificity of retrotransposons and retroviruses. Ann. Rev. Genet. 24,.491–518.

Scholer, H. R., Dressier, G. R, Balling, R., Rohdewohld, H., and Gruss, P.(1990). Oct-4: a germline-specific transcription factor mapping to the mouse t-Complex. EMBO J 9, 2185–2195.

Sharpe, N. G., Williams, D. G., and Latchman, D. S. (1990). Regulated expression of the small nuclear ribonucleoprotein particle protein SmN in embryonic stem cell differentiation. Mol. Cell. Biol. 70, 6817–6820.

Skarnes, W. C., Auerbach, B. A., and Joyner, A. L. (1992). A gene trap approach in mouse embryonic stem cells: the lacZ reporter is activated by splicing, reflects endogenous gene expression, and is mutagenic in mice. Genes Dev. 6, 903–918.

Varmus, H. (1988). Retroviruses. Science 240, 1427–1435.

von Melchner, H., DeGregori, J. V., Rayburn, H., Reddy, S., Friedel, C., and Ruley, H. E. (1992). Selective disruption of genes expressed in totipotent embryonal stem cells. Genes Dev 6, 919–927.

von Melchner, H., and Ruley, H. E. (1995). Functional analysis of the mammalian genome by gene entrapment. In Functional Analysis of the Human Genome, F. Farzane and D. N. Cooper, eds. (Oxford: Bios Scientific Publishers). 109–124.

Withers-Ward, E. S., Kitamura, Y., Barnes, J. P., and Coffin, J. M. (1994). Distribution of targets for avian retrovirus DNA integration in vivo. Genes Dev. 8, 1473–1487.

Jaenisch, R., Breindl, M., Harbers, K., Jahner, D., and Lohler, J. (1985). Retroviruses and insertional mutagenesis. Cold Spring Harb. Symp. Quant. Biol. 50, 439–445.

Friedrich, G., and Soriano, P. (1991). Promoter traps in embryonic stem cells: a genetic screen to identify and mutate developmental genes in mice. Genes Dev. 5, 1513–1523.

DeGregori, J., Russ, A., von Melchner, H., Rayburn, H., Priyaranjan, P., Jenkins, N. A., Copeland, N. G., and Ruley, H. E. (1994). A murine homolog of the yeast RNA1 gene is required for postimplantation development. Genes Dev. 8, 265–276.

We claim:

1. A system for identifying a gene expressed in a cell, comprising:
   a) a first nucleic acid sequence comprising a first reporter gene encoding a site-specific recombinase, wherein said first reporter gene is not under the control of a promoter; and
   b) a second nucleic acid sequence comprising, in order from 5' to 3',
      i. a first promoter,
      ii. a first target sequence for said recombinase,
      iii. an intervening nucleotide sequence,
      iv. a second target sequence for said recombinase, and
      v. a second reporter gene,
   wherein said first reporter gene, after being incorporated into an endogenous gene and being transcriptionally activated by an endogenous cellular promoter, is transcribed, and the encoded recombinase is produced, which encoded recombinase activates transcription of the second reporter gene, thereby allowing identification of the transcriptionally active gene under control of the endogenous cellular promoter.

2. The system of claim 1, characterized in that the recombinase is a Cre recombinase.

3. The system of claim 1, characterized in that the recombinase is a Flp recombinase.

4. The system of claim 1, characterized in that the second reporter gene encodes a protein.

5. The system of claim 4, characterized in that the protein is an IL-3.

6. The system of claim 4, characterized in that the protein is a β-galactosidase.

7. The system of claim 1, characterized in that the first promoter is a phosphoglycerate kinase (pgk) promoter.

8. The system of claim 1, wherein the intervening nucleotide sequence comprises a selectable marker.

9. The system of claim 8, characterized in that the selectable marker encodes a protein that confers antibiotic resistance.

10. The system of claim 8, characterized in that the selectable marker encodes a thymidine kinase-neomycin phosphotransferase fusion protein.

11. The system of claim 8, characterized in that the selectable marker encodes a neomycin phosphotransferase.

12. The system of claim 1 wherein the first nucleic acid sequence and the second nucleic acid sequence are physically linked.

13. The system of claim 1, wherein the first nucleic acid sequence and the second nucleic acid sequence are not physically linked.

14. A vector comprising a system of claim 12.

15. A cell, comprising a system as claimed in any one of claims 1, 2, 3, 4, 5, or 6.

16. The cell of claim 15, characterized in that said cell is selected from the group consisting of a haemopoietic precursor cell and a totipotent embryonic stem cell.

17. A cell comprising a system as claimed in any one of claims 1, 2, 4, 5, or 6, wherein the cell is a mammalian cell, wherein the first nucleic acid sequence comprises a first reporter gene encoding a Cre recombinase, wherein the second nucleic acid sequence comprises, in order from 5' to 3', a phosphoglycerate kinase (pgk) promoter, a first loxP target sequence, a nucleotide sequence encoding a thymidine kinase-neomycin transferase fusion protein (TKNeoPT), a second loxP target sequence, and a second reporter gene encoding an interleukin-3 (IL-3), wherein the Cre recombinase acts on the first and second loxp target sequences, resulting in deletion of the TKNeoPT-encoding nucleotide sequence such that the IL-3-encoding second reporter gene is brought under transcriptional control of the pgk promoter.

18. A method of identifying a transcriptionally active gene in a eukaryotic cell, comprising the steps of:

introducing a system as claimed in claim 1 into a eukaryotic cell in a population of cells;

selecting a cell from the population wherein the first reporter gene is incorporated into an endogenous gene under transcriptional control of an endogenous promoter; and identifying the endogenous gene into which the first reporter gene is incorporated.

19. The method of claim 18, wherein the transcriptionally active gene is one that is transiently expressed in the cell.

20. The method of claim 19, wherein the transiently expressed gene is selected from the group consisting of a gene involved in programmed cell death, a cell cycle gene, a DNA repair gene, and a differentiation-specific gene.

21. The system of claim 1, wherein the first nucleic acid sequence comprises a first reporter gene encoding a Cre recombinase, wherein the second nucleic acid sequence comprises, in order from 5' to 3', a phosphoglycerate kinase (pgk) promoter, a first loxP target sequence, a nucleotide sequence encoding a thymidine kinase-neomycin phosphotransferase fusion protein (TKNeoPT), a second loxP target sequence, and a second reporter gene encoding an interleukin-3 (IL-3), wherein the Cre recombinase acts on the first and second loxP target sequences, resulting in deletion of the TKNeoPT-encoding nucleotide sequence such that the IL-3-encoding second reporter gene is brought under transcriptional control of the pgk promoter.

22. A method of identifying a transcriptionally active gene in a cell, comprising:

a) introducing the system of claim 21 into an IL-3-dependent mammalian cell in a population of cells;

b) culturing the population of cells in a medium containing neomycin, thereby selecting a cell comprising the system;

c) culturing the cell selected in step (b) in IL-3-free medium, thereby selecting a cell in which the first reporter gene is integrated into a transcriptionally active endogenous gene; and d) identifying the endogenous gene into which the first reporter gene is integrated.

23. The method of claim 22, wherein the IL-3-dependent mammalian cell is an FDCP-1 cell.

24. The method of claim 22, wherein the endogenous gene is one that encodes a gene product involved in programmed cell death.

25. The system of claim 1, wherein the first nucleic acid sequence comprises a first reporter gene encoding a Cre recombinase, wherein the second nucleic acid sequence comprises, in order from 5' to 3', a phosphoglycerate kinase (pgk) promoter, a first recombinase target sequence, a nucleotide sequence encoding a thymidine kinase-neomycin phosphotransferase fusion protein (TKNeoPT), a second recombinase target sequence, and a second reporter gene encoding a β-galactosidase, wherein the Cre recombinase acts on the first and second recombinase target sequences, resulting in deletion of the TKNeoPT-encoding nucleotide sequence such that the β-galactosidase-encoding second reporter gene is brought under transcriptional control of the pgk promoter.

26. A method of identifying a gene transcriptionally activated during differentiation, comprising:

a) introducing the system of claim 25 into a totipotent embryonic stem cell in a population of totipotent embryonic stem cells;

b) culturing the population of cells in a medium containing neomycin, thereby selecting a cell that does not produce the Cre recombinase;

c) inducing the selected cell to differentiate, thereby activating a differentiation-specific gene;

d) selecting induced cells that produce β-galactosidase, thereby selecting cells comprising the first reporter gene integrated into a cellular gene; and e) identifying the cellular gene into which the first reporter gene is integrated.

* * * * *